United States Patent [19]

Gammill

[11] 4,367,341
[45] Jan. 4, 1983

[54] ANTIATHEROSCLEROTIC 7-SUBSTITUTED METHOXYFUROCHROMONES

[75] Inventor: Ronald B. Gammill, Portage, Mich.

[73] Assignee: The Upjohn Company, Kalamazoo, Mich.

[21] Appl. No.: 201,932

[22] Filed: Oct. 29, 1980

Related U.S. Application Data

[60] Division of Ser. No. 116,322, Jan. 28, 1980, Pat. No. 4,284,569, which is a continuation-in-part of Ser. No. 11,816, Feb. 13, 1979, abandoned.

[51] Int. Cl.³ .......................................... C07D 311/78
[52] U.S. Cl. .................................................... 549/387
[58] Field of Search ........... 260/345.2, 239.95, 326.34, 260/326.5 E, 326.8; 544/150, 60, 96, 378; 546/197; 549/387

[56] References Cited

U.S. PATENT DOCUMENTS

| | | | |
|---|---|---|---|
| 2,680,119 | 6/1954 | Robertson et al. | 260/345.2 |
| 2,736,727 | 2/1956 | Fourneau | 260/345.2 |
| 2,855,406 | 10/1958 | Dann | 260/345.2 |
| 3,099,660 | 7/1963 | Dann | 260/345.2 |
| 3,483,194 | 12/1969 | Musante et al. | 260/345.2 |

OTHER PUBLICATIONS

Abu—Shady et al., J. Pharm. Belg., 33, 397, (1978).
Schonberg et al., JACS, 11, 5439, (1955).
Mustafa et al., J. Org. Chem., 26, 886, (1961).
Musante et al., Pharmaco (Pavie), Ed. Sci., 15, 81, (1960).
Abu—Shady, U.A.R. J. Pharm. Sci., 11, 283, (1970).
Fabbrini, Ann. Chim., (Rome), 46, 130, (1956).
Mustafa, "Furopyrans and Furopyrones," John Wiley and Sons, Inc., New York, 1967, pp. 102–159.

*Primary Examiner*—Nicky Chan
*Attorney, Agent, or Firm*—Robert A. Armitage

[57] ABSTRACT

The present invention provides novel 7-substituted methoxyfurochromones, which are useful as antiatherosclerotic agents.

9 Claims, No Drawings

ANTIATHEROSCLEROTIC 7-SUBSTITUTED METHOXYFUROCHROMONES

DESCRIPTION

CROSS REFERENCE TO RELATED APPLICATIONS

This application is a divisional of copending application Ser. No. 116,322, filed Jan. 28, 1980, now U.S. Pat. No. 4,284,569, issued Aug. 18, 1981, which is a continuation-in-part of application Ser. No. 11,816, filed Feb. 13, 1979, now abandoned.

BACKGROUND OF THE INVENTION

The present invention relates to novel furochromones which are khellin analogs and useful as antiatherosclerotic agents. Khellin is 7-methyl-4,9-dimethoxyfurochromone. Most particularly the present invention relates to 7-substituted methoxyfurochromones, the pharmaceutical use and preparation of which is incorporated by reference here from U.S. Pat. No. 4,284,569.

PRIOR ART

Extensive pharmacological uses for khellin and related substances are known. Khellin analogs are also known in the art. These analogs include:

(i) 6-chloromethyl- and 6-iodomethylfurochromones, see Abu-Shady, H., UAR J. Pharm. Sci. 11:283 (1970);

(ii) 6,7-dihalo-6,7-dihydrofurochromones, see Fabbrini, L., Ann. Chim. (Rome) 46:130 (1956);

(iii) 7-ethyl-, 7-propyl-, and 7-ethoxycarbonyl-4,9-dimethoxyfurochromones, see Schonberg, A., et al., JACS 72; 1611 (1950);

(iv) 7- -pyridyl analogs of 4,9-dimethoxyfurochromone, see Schonberg, A., et al., JACS 77:5439 (1955);

(v) 7-furanyl- and 7-isoxazolyl analogs of 4,9-dimethoxyfurochromone, see Musante, C., et al., Pharmaco (Pavie) Ed. Sci. 15:81 (1960);

(vi) 7-carboxaldehyde analogs of 4,9-dimethoxyfurochromone, see Mustafa, A. et al., J. Org. Chem. 26:886 (1961); and (vii) alkyl and alkoxy analogs described in U.S. Pat. Nos. 3,099,660; 2,680,119 and 2,666,766.

Other furochromones are described in U.S. Pat. Nos. 3,483,194; 2,855,406; and 2,736,727. 4-Methoxy-7-(substituted)aminomethylfurochromones are also known in the art. See Abu-Shady, H., et al., J. Pharm. Belg. 33:397 (1978).

SUMMARY OF THE INVENTION

The present invention particularly provides a furochromone of formula VII

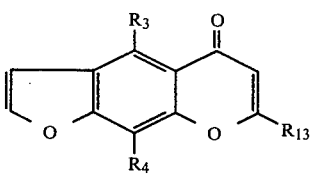

wherein $R_{13}$ is:
(a) trifluoromethyl;
(b) phenoxymethyl;
(c) phenylthiomethyl;
(d) phenoxymethyl or phenylthiomethyl substituted by chloro, fluoro, trifluoromethyl, alkyl of one to 3 carbon atoms, or alkoxy of one to 3 carbon atoms; or
(e) cycloalkyl of 3 to 10 carbon atoms, inclusive; and wherein one of $R_3$ and $R_4$ is methoxy and the other is methoxy or hydrogen.

These compounds are useful as anthiathersclerotic agents as described in U.S. Pat. No. 4,284,569.

DESCRIPTION OF THE PREFERRED EMBODIMENTS

The present invention particularly relates to: 4,9-dimethoxy-7-phenylthiomethylfurochromone, and 4,9-dimethoxy-7-trifluoromethylfurochromone.

I claim:

1. A fruochromone of Formula VII

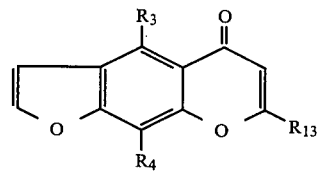

wherein $R_{13}$ is:
(a) trifluoromethyl;
(b) phenoxymethyl;
(c) phenylthiomethyl;
(d) phenoxymethyl or phenylthiomethyl substituted by chloro, fluoro, trifluoromethyl, alkyl of 1 to 3 carbon atoms, or alkoxy of 1 to 3 carbon atoms; or
(e) cycloalkyl of 3 to 10 carbon atoms, inclusive; and wherein one of $R_3$ and $R_4$ is methoxy and the other is methoxy or hydrogen.

2. A furochromone according to claim 1, wherein $R_3$ is methoxy, $R_4$ is hydrogen.

3. A compound according to claim 1, wherein $R_3$ is hydrogen and $R_4$ is methoxy.

4. A compound according to claim 1, wherein both $R_3$ and $R_4$ are methoxy.

5. 4,9-dimethoxy-7-cyclopropylfurochromone, a compound according to claim 4, wherein $R_{13}$ is cyclopropyl.

6. A compound according to claim 4 wherein $R_{13}$ is phenoxymethyl or phenylthiomethyl and wherein the phenyl ring is optionally substituted by chloro, fluoro, trifluoromethyl, alkyl of 1 to 3 carbon atoms, or alkoxy of 1 to 3 carbon atoms.

7. 4,9-dimethoxy-7-phenoxymethylfurochromone, a compound according to claim 6, wherein $R_{13}$ is phenoxymethyl.

8. 4,9-dimethoxy-7-phenylthiomethylfurochromone, a compound according to claim 6, wherein $R_{13}$ is phenylthiomethyl.

9. 4,9-dimethoxy-7-trifluoromethylfurochromone, a compound according to claim 4, wherein $R_{13}$ is trifluoromethyl.

* * * * *